United States Patent
Tan et al.

(10) Patent No.: US 11,413,339 B2
(45) Date of Patent: Aug. 16, 2022

(54) WHOLE-CELL TUMOR VACCINE BASED ON PRINCIPLE OF EXTRACELLULAR TRAP AND METHOD OF MAKING SAME

(71) Applicant: Hainan Medical University, Hainan (CN)

(72) Inventors: Guang-Hong Tan, Hainan (CN); Feng-Ying Huang, Hainan (CN); Liming Zhang, Hainan (CN); Zhuoxuan Lv, Hainan (CN); Ying-Ying Lin, Hainan (CN)

(73) Assignee: Hainan Medical University, Haikou (CN)

( * ) Notice: Subject to any disclaimer, the term of this patent is extended or adjusted under 35 U.S.C. 154(b) by 395 days.

(21) Appl. No.: 16/842,736

(22) Filed: Apr. 7, 2020

(65) Prior Publication Data
US 2020/0345822 A1    Nov. 5, 2020

(30) Foreign Application Priority Data

May 5, 2019  (CN) .......................... 201910369398.9

(51) Int. Cl.
| | | |
|---|---|---|
| *A01N 63/00* | (2020.01) | |
| *A61K 39/00* | (2006.01) | |
| *A61P 35/00* | (2006.01) | |
| *A61K 39/39* | (2006.01) | |
| *C12N 5/09* | (2010.01) | |

(52) U.S. Cl.
CPC .......... *A61K 39/0011* (2013.01); *A61K 39/39* (2013.01); *A61P 35/00* (2018.01); *C12N 5/0693* (2013.01); *A61K 2039/5152* (2013.01); *A61K 2039/53* (2013.01); *A61K 2039/54* (2013.01); *A61K 2039/55561* (2013.01); *A61K 2039/575* (2013.01)

(58) Field of Classification Search
CPC .................................................. A61K 39/0011
See application file for complete search history.

(56) References Cited

U.S. PATENT DOCUMENTS

2011/0027321 A1    2/2011 Lu et al.

FOREIGN PATENT DOCUMENTS

| CN | 1548537 A | 11/2004 |
| CN | 103861107 A | 6/2014 |

OTHER PUBLICATIONS

Goldstein et al (Blood vol. 117, No. 1, pp. 118-127) (Year: 2011).*

* cited by examiner

*Primary Examiner* — Albert M Navarro

(57) ABSTRACT

Disclosed are a whole-cell tumor vaccine based on the principle of extracellular traps and a method of making the same, where a CpG ODN network similar to the extracellular trap in structure is formed on the tumor cell surface. The tumor cells are coated with a histone and CpG ODN to form the CpG ODN-coated tumor cells, which are inactivated to produce the whole-cell tumor vaccine. The vaccine of the invention, after injected to tumor model mice, can induce the occurrence of effective immune response to achieve the effective treatment for tumors.

10 Claims, 3 Drawing Sheets

WHOLE-CELL TUMOR VACCINE BASED ON PRINCIPLE OF EXTRACELLULAR TRAP AND METHOD OF MAKING SAME

CROSS-REFERENCE TO RELATED APPLICATIONS

This application claims the benefit of priority from Chinese Patent Application No. 201910369398.9, filed on May 5, 2019. The content of the aforementioned application, including any intervening amendments thereto, is incorporated herein by reference.

TECHNICAL FIELD

This application relates to tumor vaccine and preparation methods therefor, and more particularly to a novel tumor cell vaccine based on the principle of extracellular trap and a method of making the same, where the method mainly includes: preparing a mimic extracellular trap mainly composed of CpG oligodeoxynucleotide (CpG ODN, pertaining to DNA) and histones on the surface of tumor cells and inactivating the obtained tumor cells to prepare the whole-cell tumor vaccine capable of treating tumors.

BACKGROUND

Whole-cell tumor vaccine, as a novel tumor vaccine, has been widely investigated at home and abroad and has a bright application prospect. However, since the immune system fails to exert effective immunological effect on the autologous tumor cells, the autologous tumor cells cannot be directly used in the preparation of a vaccine. It has been reported that the tumor cells can be transformed or modified by transferring cytokines capable of enhancing the activity and function of immunocytes (such as one or more of granulocyte-macrophage colony-stimulating factor, fibroblast activation protein and interleukin-2) into tumor cells using genetic recombination technology to enhance the immune response. Though some tumor cell vaccines have even been subjected to clinic trial, the results are not very satisfactory. Therefore, there is still an urgent need to develop a better technique or strategy to prepare a novel whole-cell tumor vaccine.

The concept of "Extracellular traps" is originated from Neutrophil extracellular traps since this phenomenon is first observed in neutrophils. However, recently, this phenomenon has also been discovered in other immune cells such as monocytes, macrophages, eosinophils, basophils and NK cells, so that it is collectively referred to "Extracellular traps". Specifically, the extracellular trap refers to a reticular fiber structure released by immune cells (such as the above-mentioned types of cells) in a pre-death state, where this reticular fiber structure is mainly composed of intranuclear substances, including concentrated DNA, histones and granular proteins. This reticular structure is capable of enclosing pathogenic microorganisms and even some autologous pathological cells to prompt immune cells to phagocytize and clear the enclosed pathogenic microorganisms and/or cells. Moreover, during the phagocytosis and clearance, corresponding antigens are also processed and presented to further activate and increase the specific immune response for the phagocytized microorganisms and/or cells. It has been recently found that the production of characteristic antinuclear antibodies in patients suffering from an autoimmune disease is related to the extracellular trap. However, there is still lack of technical solutions to effectively prepare tumor cell vaccines using the principle or components of the extracellular trap.

SUMMARY

An object of the invention is to provide a novel whole-cell tumor vaccine based on a principle of extracellular traps and a method of making the same, where the extracellular trap used herein is mainly composed of DNA (CpG ODN suitable as an immune adjuvant is selected herein) and histones, which are coated on the surface of tumor cells to form an extracellular trap (ET)-like CpG ODN network. These tumor cells coated with CpG ODN and histones on the surface are referred to as "CpG ODN-coated tumor cells" herein. As demonstrated by specific experiments that the CpG ODN-coated tumor cells of the invention, after used as a vaccine to be injected subcutaneously (or intravascularly, intramuscularly or intraperitoneally) in tumor model mice, can induce immune system to generate an effective immune response, enabling the effective treatment of tumors. Therefore, the invention has a good clinical application prospect.

The development of this invention is based on the following principles. It has been currently found that the production of characteristic antinuclear antibodies in patients with autoimmune diseases is related to the extracellular traps, indicating that the extracellular traps are capable of inducing the immune system to produce a DNA vaccine adjuvant having specific immune response to the encapsulated cells, which is also a ligand of Toll-like receptor 9 (TLR9), so that it can be recognized by TLR9 on antigen-presenting cells such as dendritic cells (DCs) during the stage of pathogen infection to promote the maturation of DCs. Then the matured DCs can promote the immune response of $CD8^+T$ cells, NK and Th1 cells by secreting cytokines such as INF-α. Based on the above, CpG ODN has been used as an immune adjuvant in clinical trials and in the development of various vaccines. Some immune checkpoint molecules expressed on the tumor surface such as PD-L1 and CD47 can be recognized by molecules on immune cells (such as PD-1 and SIRPa) to cause immune cells to lose their response to tumor cells. Based on the principle of extracellular traps and the characteristic that the tumor cell surface and CpG ODN both carry negative charges, the invention proposes a method of preparing a novel vaccine having therapeutic effect on tumors, in which a DNA (CpG ODN) and histones are coated on the surface of tumor cells to form an extracellular trap (ET)-like CpG ODN network to obtain CpG ODN-coated tumor cells, which are then inactivated to prepare the desired vaccine. The vaccine is primarily composed of CpG ODN, histones and tumor cells. The prepared vaccine can induce the immune cells to generate specific immune response to tumor cells through the following two processes: (1) CpG ODN on the surface of tumor cells is a danger signal and can induce specific immune responses through the TLR9 signaling pathway; and (2) the CpG ODN network coating tumor cells may cover checkpoint molecules such as PD-L1 and CD47 on the cell surface, blocking the signal pathways of PD-1/PD-L1 and CD47/SIRPa and also promoting the immune response. After inactivated, the CpG ODN-coated tumor cells can be injected into tumor model mice as a tumor vaccine to induce the immune system to produce the tumor cell-specific immune response, enabling a desirable treatment of tumors. The invention prepares a tumor vaccine from CpG ODN-coated tumor cells, which is a new method in the field of tumor vaccine preparation and has a brilliant clinical application prospect.

Technical solutions of the invention are described as follows.

In a first aspect, the invention provides a novel whole-cell tumor vaccine based on a principle of extracellular traps, comprising: DNA, a histone and tumor cells;

wherein the DNA is CpG oligodeoxynucleotide (ODN);

the tumor cells are isolated and extracted from any tumor tissues;

the CpG ODN and the histone are coated on a surface of the tumor cells to form an extracellular trap (ET)-like CpG ODN network to obtain CpG ODN-coated tumor cells.

In an embodiment, a membrane-associated cytoskeleton of the tumor cells and the CpG ODN both contain a phosphoric acid; the surface of the tumor cells and the CpG ODN are both negatively charged; the histone is positively charged due to the presence of a large amount of arginine and lysine; and the CpG ODN is bound to the surface of the tumor cells through the histone to form the CpG ODN-coated tumor cells.

In an embodiment, the tumor cells are isolated and extracted from in-vitro tumor tissues from a patient with a tumor and thus prepared whole-cell tumor vaccine is an individualized vaccine for the patient.

In a second aspect, the invention provides a method of preparing the above whole-cell tumor vaccine, comprising:

(1) culturing the tumor cells to logarithmic phase; harvesting and counting the tumor cells; and adjusting the tumor cells with phosphate buffered saline (PBS) to a concentration of $1\times10^6/100$ µL; wherein the PBS may be replaced with a solution having an osmotic pressure the same as or similar to human body fluid, such as normal saline;

(2) dissolving the histone with normal saline or phosphate buffered saline to produce a histone solution; adding the tumor cells to the histone solution; gently shaking the reaction mixture at room temperature for 10-20 min; washing the reaction mixture three times with PBS to remove the unconjugated histone; dissolving the CpG ODN with PBS to produce a CpG ODN solution; adding the histone-conjugated tumor cells to the CpG ODN solution; gently shaking the reaction mixture at room temperature for 10-20 min; and washing the reaction mixture three times with PBS to remove the unconjugated CpG ODN; wherein a ratio of the histone to the tumor cells is 5-10 (mg): $2\times10^6$ (cells); and a ratio of CpG ODN to the tumor cells is 5-10 (µg): $2\times10^6$ (cells);

(3) centrifuging the reaction mixture obtained in step (2); discarding a supernatant to collect CpG ODN-coated tumor cells; washing the CpG ODN-coated tumor cells twice with PBS to remove the free CpG ODN; and dissolving the CpG ODN-coated tumor cells to a desired concentration; and (4) inactivating the CpG ODN-coated tumor cells in the CpG ODN-coated tumor cell solution at an irradiation intensity of 50-100 Gy using an X-ray instrument to ensure that no growth, proliferation and metastasis are observed after the injection of the CpG ODN-coated tumor cells to produce the desired whole-cell tumor vaccine.

In an embodiment, the inactivated CpG ODN-coated tumor cells as the whole-cell tumor vaccine are administered to mice by dissolving the cells in 80-100 µL of phosphate buffered solution, and injecting the cells into mice with each mouse being injected with $3\times10^5$-$5\times10^5$ cells each time; and the injection route may be subcutaneous, intramuscular, intravascular or intraperitoneal.

In an embodiment, step (2) comprises:

dissolving the histone with PBS to produce the histone solution; and adjusting the histone solution with 1 M sodium hydroxide to pH 7-9 to render the histone solution clear and transparent; and wherein step (2) is preferably performed at 4° C. in a shaker; and the PBS is preferably pre-cooled at 4° C.

In an embodiment, step (2) comprises:

dissolving the histone with PBS to produce the histone solution;

dissolving the CpG ODN with PBS to produce the CpG ODN solution;

adjusting the histone solution with 1 M sodium hydroxide to pH 7-9 to render the histone solution clear and transparent; and mixing the adjusted histone solution with the tumor cells for 10-20 min to produce histone-conjugated tumor cells;

washing the reaction mixture three times with PBS to remove the unconjugated histone; and adding the CpG ODN solution to the histone-conjugated tumor cells, wherein a ratio of the histone to the tumor cells is 5-10 (mg):$10^3$-$10^4$ (cells); and a ratio of the µg ODN to the tumor cells is 5-10 (µg): $10^3$-$10^4$ (cells).

In an embodiment, in step (3), the centrifugation is performed at 500-800×g; and during the washing, a centrifuge tube is gently rotated for 3-5 circles.

In an embodiment, in step (4), the inactivated tumor cells are adjusted with PBS to preferably $3\times10^5$-$5\times10^5$ cells/100 µL, and the concentration can be adjusted according to the amount of cells for injection. Preferably, the final injection volume is 80-100 µL.

Compared to the prior art, the invention has the following beneficial effect.

The invention develops a novel method based on the principle of extracellular traps to prepare a whole-cell tumor vaccine, which has a good clinical application prospect. Specifically, the CpG ODN-coated tumor cells prepared herein are inactivated and then vaccinated subcutaneously, intramuscularly, intravascularly or intraperitoneally to tumor model mice, which can induce the occurrence of effective immune response, achieving the effective treatment for tumors and having a good clinical application prospect. In actual application, the tumor cells can be isolated from tumor tissues of a patient with a tumor and then accordingly prepared into the specific whole-cell tumor vaccine using the method of the invention. Therefore, the invention facilitates the treatment for human tumors.

BRIEF DESCRIPTION OF THE DRAWINGS

The invention will be further illustrated with reference to the accompanying drawings and embodiments.

DETAILED DESCRIPTION OF EMBODIMENTS

The invention will be further described below with reference to the embodiments, but these embodiments are not intended to limit the invention. Various modifications and changes made based on the content disclosed herein should fall within the scope of the invention.

Figure 1:
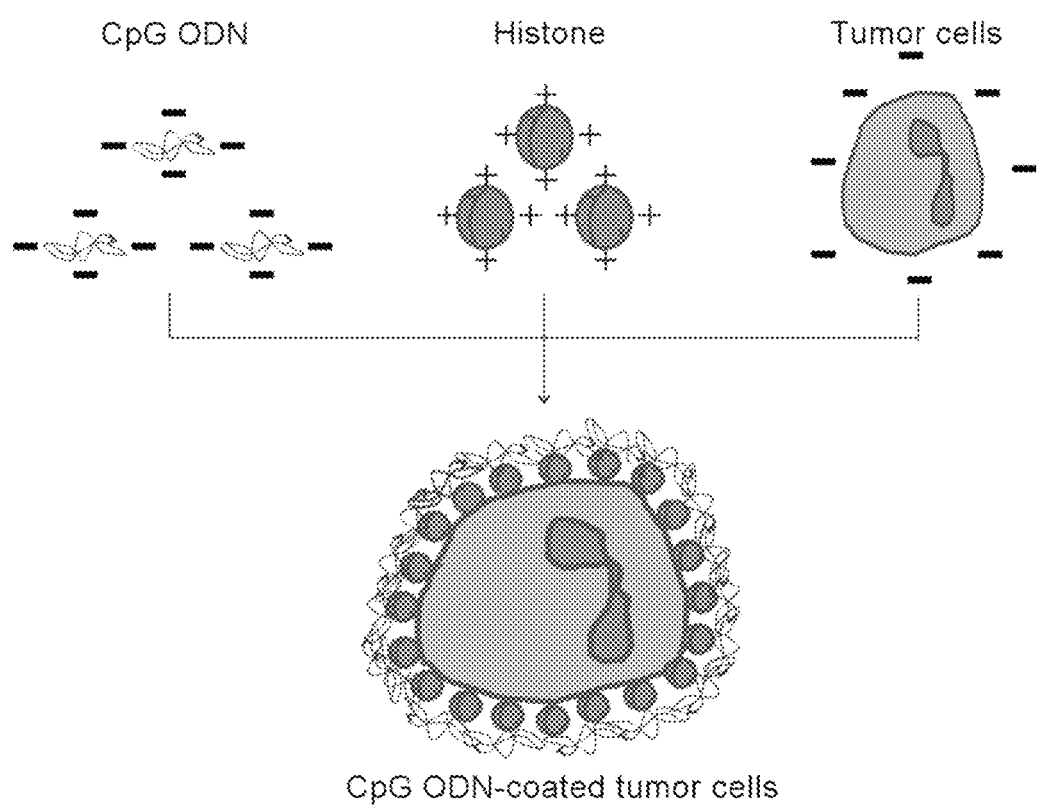
FIG. 1 schematically shows the preparation of CpG ODN-coated tumor cells of the invention.

FIG. 1 schematically shows the preparation of CpG ODN-coated tumor cells of the invention. As shown in FIG. 1, a membrane-associated cytoskeleton of the tumor cells and the CpG ODN both contain phosphate groups; the surface of the tumor cells and the CpG ODN are both negatively charged; the histone is positively charged due to the presence of a large amount of arginine and lysine; the CpG ODN is bound to the surface of the tumor cells through the histone to produce the CpG ODN-coated tumor cells, which are then inactivated to be used as a tumor vaccine.

Specifically, the CpG ODN and the histone are coated on the surface of the tumor cells to form an extracellular trap (ET)-like CpG ODN network. Some immune cells (such as neutrophils and macrophages) can use intracellular DNA (CpG ODN is a special form of DNA), histones and other components to form a network structure before the death, which can enclose pathogenic substances such as bacteria, parasites, viruses and disease cells (including tumor cells). Then other immune cells are induced to eliminate these enclosed substances to further cause immune response. The tumor cells coated with a network of the CpG ODN and histone are referred to as "CpG ODN-coated tumor cells" herein.

1. Culturing and Harvesting of Tumor Cells

Murine colon cancer CT26 cells derived from American Type Culture Collection (ATCC) were adopted herein and stored in liquid nitrogen before use. 0.27 g of potassium dihydrogen phosphate, 1.42 g of disodium hydrogen phosphate, 8 g of sodium chloride and 0.2 g of potassium chloride were mixed and added with ultrapure water to 1 L to produce a PBS (pH 7.4). The PBS was sterilized under high temperature before use.

The CT26 cells were transferred from the liquid nitrogen tank and immediately placed in a 37° C. water bath under repeated shaking for about 1-2 min until they were completely melted. The obtained cell suspension was centrifuged at 2000 rpm for 5 min and the supernatant was removed. The cells were added with RPMI 1640, fetal bovine serum, antibiotics and growth factors (referring to the instruction of the cell product for detailed information), mixed uniformly, added to a tissue culture flask and cultured at 37° C. and 5% $CO_2$. The medium was replaced every other 1-2 day. After the cells grew to occupy about 80% of the culture flask, the medium was removed and the cells were washed twice with PBS, digested with 0.25% trypsin and centrifuged at 2000 rpm for 5 min. The supernatant was discarded, and the cells were washed twice with PBS and counted. After that, the cells were adjusted with PBS to a concentration of $1\times10^6$ cells/100 μL for the subsequent coating of CpG ODN.

2. Preparation of CpG ODN-Coated Tumor Cells

In the preparation of CpG ODN-coated tumor cells, the CpG ODN was purchased from Invitrogen Co., Inc. and the histone was purchased from Sangon Biotech (Shanghai) Co., Inc.

EXAMPLE (1) 1 mg of the histone was completely dissolved with 1.8 mL of PBS under shaking. If the histone cannot be completely dissolved, the mixture was adjusted to pH 9 with 1 M sodium hydroxide to render it clear and transparent. Then the histone solution was added with PBS to a final volume of 2 mL. The histone solution was added with $2\times10^7$ CT26 tumor cells and shaken at room temperature for 10-20 min.

(2) The reaction mixture was centrifuged at 3000 rpm for 5 min, and the supernatant containing the free histone was discarded. The cells were washed twice with PBS and dissolved in 2 mL of PBS. The cell suspension was added with 1-5 μg of the CpG ODN and shaken at room temperature for 10-20 min to allow the CpG ODN to completely bind to the histone on the cell surface.

(3) The reaction mixture was centrifuged and the supernatant containing the free CpG ODN was removed. The cells were washed twice with PBS and then adjusted with PBS to a concentration of $1\times10^5$ cells/100 μL to produce the CpG ODN-coated CT26 tumor cell suspension.

3. Verification

Figure 2A:
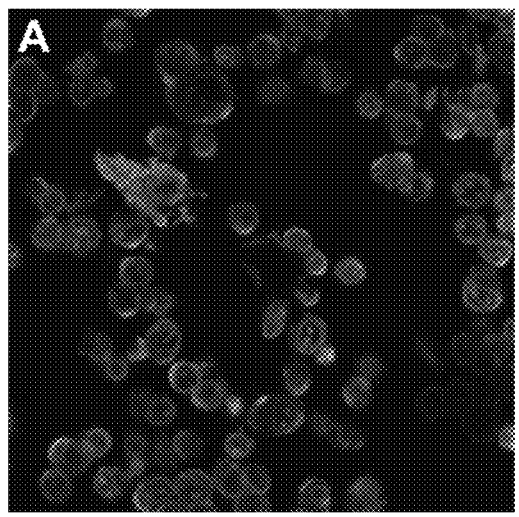
FIG. 2A shows the CpG ODN of the CpG ODN-coated tumor cells under a confocal microscope.
Figure 2B:
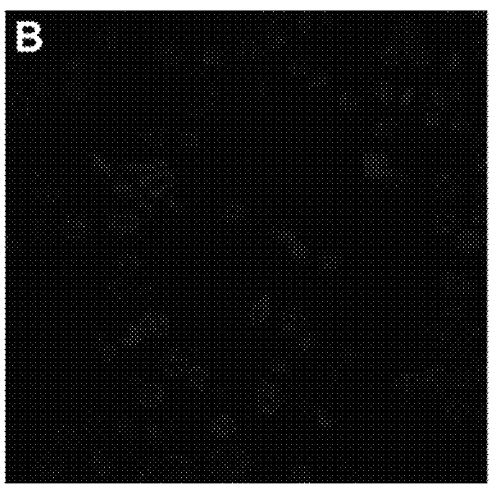
FIG. 2B shows nuclei of the CpG ODN-coated tumor cells under the confocal microscope.
Figure 2C:
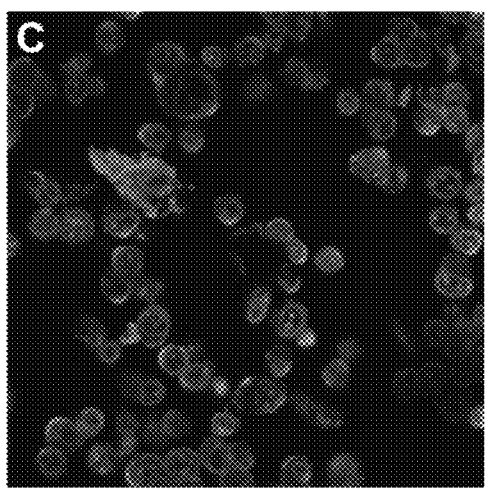
FIG. 2C shows the superimposition of FIGS. 2A and 2B.

In order to verify whether the CpG ODN-coated tumor cells has been successfully prepared above, the CpG employed in the preparation was labeled with fluorescein isothiocyanate (FITC) which was capable of emitting green fluorescence. 100 μL of the above-prepared CpG ODN-coated CT26 tumor cell suspension was placed in a special detection dish of a confocal microscope (Olympus FV100) and observed whether there was green fluorescence emitted from the detected cells. Moreover, the cells were also stained with DAPI to allow the nuclei to emit blue fluorescence before the detection, so that the green fluorescence and the blue fluorescence were respectively observed in the same view. Then the green and blue fluorescence images were superimposed to determine the relationship between the green fluorescence (CpG) and the blue fluorescence (nucleus). Since DAPI was capable of staining all nuclear DNA into blue and the positively-prepared CpG ODN-coated CT26 tumor cells should be observed by the confocal microscope to have green fluorescence on the surface, the green fluorescence should be at the periphery of the nucleus (blue fluorescence). FIGS. 2A and 2B were respectively the green and blue fluorescence images, and FIG. 2C showed the superimposition of the green and blue fluorescence images. It can be demonstrated by FIGS. 2A-2C that the CpG ODN-coated CT26 tumor cells were successfully prepared herein.

4. Preparation of Vaccine from Inactivated CpG ODN-Coated Tumor Cells (1) The CpG ODN-coated CT26 tumor cells prepared above were inactivated at an irradiation intensity of 50-100 Gy using an X-ray instrument (Rad Source RS2000) to ensure that no growth, proliferation and metastasis were observed after the CpG ODN-coated tumor cells were vaccinated, achieving the safe application.

(2) The inactivated CpG ODN-coated CT26 tumor cells were injected as a vaccine subcutaneously, intramuscularly, intravascularly or intraperitoneally to mice, where individual mice were injected with $3\times10^5$-$5\times10^5$ CpGODN-coatedtumor cells each time.

Figure 3A:
FIG. 3A shows mice in the group treated with the CpG ODN-coated tumor cells according to an embodiment of the invention, where 4 of the 5 mice from the treatment group involve absolutely no tumor growth, and the other one has a tumor significantly smaller in size than the mice in the control.
Figure 3B:
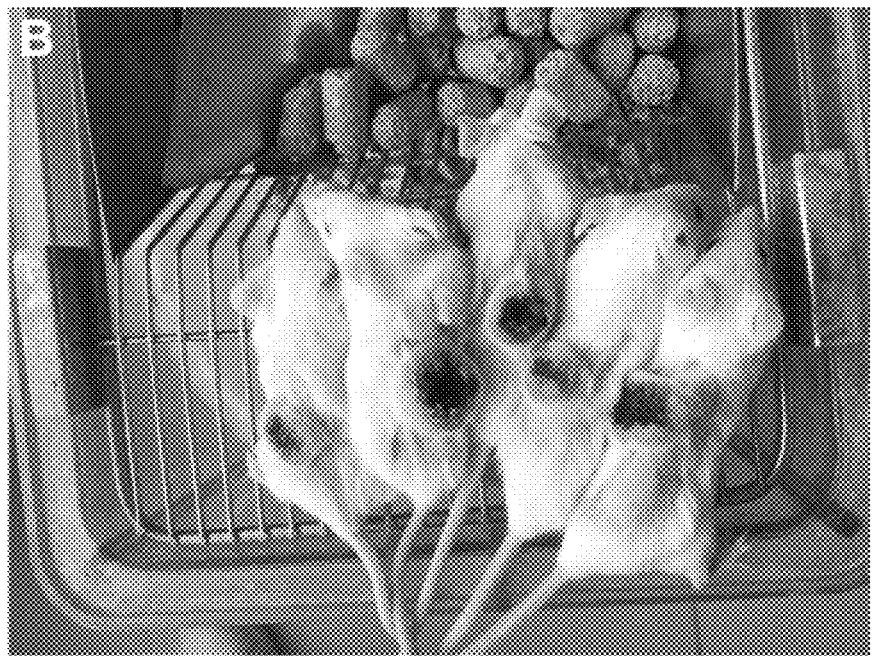
FIG. 3B shows the control group in which the mice were not treated.

5. Therapeutic Effect of CpG ODN-Coated Whole-Cell Tumor Vaccine on CT26-Bearing Mice The verification was performed in accordance with the precautionary procedures. 10 female BALB/c mice, aged 6-8 weeks, were selected and divided into two groups, i.e., treatment group and control group. Mice in the treatment group were injected subcutaneously with $5\times10^5$ of the inactivated CpG ODN-coated CT26 colon cancer cells (dissolved in 100 μL of PBS) at the upper right side of the back. One week later, $2\times10^6$ murine CT26 colon cancer cells were injected subcutaneously on the lower left side of the back of mice in the two groups to establish a tumor model (i.e., transplantation of the tumor), and then the tumor growth in mice was monitored. The mice were sacrificed 28 days after injection of tumor cells. The serum was collected and detected for the specific antibodies against the CT26 colon cancer cells, and the spleen lymphocytes were used as effector cells in the killing experiments of the CT26 colon cancer cells. It can be seen from the results that almost no tumor growth was observed in 4 of the 5 mice in the treatment group, and the tumor in the other one was significantly smaller than that in the mice of the control (as shown in FIGS. 3A-3B). Moreover, with regard to the mice from the treatment group, the specific antibodies against the CT26 colon cancer cells were found in the serum thereof, and their lymphocytes had significant killing effect on the CT26 colon cancer cells. These experimental results demonstrated that the CpG ODN-coated CT26 whole-cell tumor vaccine can effectively induce the immune response specifically against the CT26 colon cancer cells, effectively inhibiting the growth of the murine colon cancer tumors.

Described above are merely preferred embodiments of the invention, and these embodiments are not intended to limit the invention. Various modifications, changes and replacements made based on the content of the invention should fall within the scope of the invention.

What is claimed is:

1. A whole-cell tumor vaccine, comprising: DNA, a histone and tumor cells;
    wherein the DNA is CpG oligodeoxynucleotide (ODN);
    the tumor cells are isolated and extracted from any tumor tissues;
    the CpG ODN and the histone are coated on a surface of the tumor cells to form an extracellular trap (ET)-like CpG ODN network to obtain CpG ODN-coated tumor cells; and
    the CpG ODN-coated tumor cells are inactivated to produce the whole-cell tumor vaccine.

2. The whole-cell tumor vaccine of claim 1, wherein a membrane-associated cytoskeleton of the tumor cells and the CpG ODN both contain phosphate groups; the surface of the tumor cells and the CpG ODN are both negatively charged; the histone contains arginine and lysine and is positively charged; the CpG ODN is linked to the surface of the tumor cells through the histone, so that the CpG ODN and the histone are coated on the surface of the tumor cells to obtain the CpG ODN-coated tumor cells.

3. The whole-cell tumor vaccine of claim 1, wherein the tumor cells are colon cancer CT26 cells; and the whole-cell tumor vaccine, after the tumor cells therein are adjusted in number, is injected to mice.

4. A method of preparing the whole-cell tumor vaccine of claim 1, comprising:
    (1) culturing the tumor cells to logarithmic phase; harvesting and counting the tumor cells; and adjusting a concentration of the tumor cells with normal saline or phosphate buffered saline;
    (2) dissolving the histone with normal saline or phosphate buffered saline to produce a histone solution; adding the tumor cells to the histone solution to produce histone-conjugated tumor cells; gently shaking the reaction mixture at room temperature for 10-20 min; washing the reaction mixture three times with PBS to remove the unconjugated histone; dissolving the CpG ODN with PBS to produce a CpG ODN solution; adding the histone-conjugated tumor cells to the CpG ODN solution; and gently shaking the reaction mixture at room temperature for 10-20 min; wherein a ratio of the histone to the tumor cells is 5-10 (mg):$2\times10^6$ (cells); and a ratio of CpG ODN to the tumor cells is 5-10 (μg): $2\times10^6$ (cells);
    (3) centrifuging the reaction mixture obtained in step (2); discarding a supernatant and washing the tumor cells with PBS to remove the free CpG ODN to produce CpG ODN-coated tumor cells; and
    (4) inactivating the CpG ODN-coated tumor cells to produce the whole-cell tumor vaccine.

5. The method of claim 4, wherein the tumor cells are isolated and extracted from in-vitro tumor tissues from a patient with a tumor and thus prepared whole-cell tumor vaccine is an individualized vaccine for the patient.

6. The method of claim 4, wherein the inactivated CpG ODN-coated tumor cells as the whole-cell tumor vaccine are administered to mice by dissolving the cells in 80-100 μL of phosphate buffered solution, and injecting the cells into mice with each mouse being injected with $3\times10^5$-$5\times10^5$ cells each time; and
    wherein the injection route is subcutaneous, intramuscular, intravascular or intraperitoneal.

7. The method of claim 4, wherein step (2) further comprises:
    adjusting the histone solution with 1 M sodium hydroxide to pH 7-9 to render the histone solution clear and transparent.

8. The method of claim 4, wherein step (2) comprises:
    adjusting the histone solution with 1 M sodium hydroxide to pH 7-9 to render the histone solution clear and transparent; and
    mixing the adjusted histone solution with the tumor cells for 10-20 min.

9. The method of claim 4, wherein in step (3), the centrifugation is performed at 500-800×g, and during the washing, centrifuge tubes are rotated gently for 3-5 circles.

10. The method of claim 4, wherein in step (4), the inactivation is performed by X-ray irradiation, and the whole-cell tumor vaccine is adjusted with phosphate buffered saline to a concentration for injection.

* * * * *